(12) United States Patent
Wen et al.

(10) Patent No.: US 11,945,766 B2
(45) Date of Patent: Apr. 2, 2024

(54) ACETONITRILE PURIFICATION PROCESS FOR ULTRAHIGH PERFORMANCE LIQUID CHROMATOGRAPHY-MASS SPECTROMETER

(71) Applicant: FTSCI (HUBEI) BIOTECH CO., LTD., Xiaogan (CN)

(72) Inventors: Sheng Wen, Xiaogan (CN); ZhengChong Zhao, Xiaogan (CN); ChunLi Gong, Xiaogan (CN); Fan Cheng, Xiaogan (CN); Hai Liu, Xiaogan (CN); FuQiang Hu, Xiaogan (CN)

(73) Assignee: FTSCI (HUBEI) BIOTECH CO., LTD.

( * ) Notice: Subject to any disclaimer, the term of this patent is extended or adjusted under 35 U.S.C. 154(b) by 0 days.

(21) Appl. No.: 17/314,079

(22) PCT Filed: May 7, 2020

(86) PCT No.: PCT/CN2020/088936
§ 371 (c)(1),
(2) Date: May 7, 2021

(87) PCT Pub. No.: WO2021/223145
PCT Pub. Date: Nov. 11, 2021

(65) Prior Publication Data
US 2023/0073691 A1    Mar. 9, 2023

(30) Foreign Application Priority Data

May 6, 2020 (CN) .......................... 202010371683.7

(51) Int. Cl.
*C07C 253/34* (2006.01)
*C07C 255/07* (2006.01)

(52) U.S. Cl.
CPC .......... *C07C 253/34* (2013.01); *C07C 255/07* (2013.01)

(58) Field of Classification Search
None
See application file for complete search history.

(56) References Cited

FOREIGN PATENT DOCUMENTS

| CN | 102432499 A |   | 5/2012  |           |
|----|-------------|---|---------|-----------|
| CN | 102746187 A |   | 10/2012 |           |
| CN | 102775327 A |   | 11/2012 |           |
| CN | 104744299 A |   | 7/2015  |           |
| CN | 107382776 A | * | 11/2017 | C07C 253/34 |
| CN | 107382776 A |   | 11/2017 |           |
| CN | 209602424 U | * | 11/2019 | C07C 253/34 |
| CN | 209602424 U |   | 11/2019 |           |

OTHER PUBLICATIONS

Banat et al. "Adsorptive Distillation Using Molecular Sieves and Low-cost Biobased Adsorbents for the Break-up of the Isopropanol-Water Azeotrope" Adsorption Science & Technology, vol. 21, No. 9, pp. 821-830. (Year: 2003).*

* cited by examiner

*Primary Examiner* — Joseph R Kosack
(74) *Attorney, Agent, or Firm* — Jose Cherson Weissbrot

(57) ABSTRACT

The present invention relates to the technical field of acetonitrile refining, and in particular, to an improved acetonitrile purification process for an ultrahigh performance liquid chromatography-mass spectrometer. The present invention provides an acetonitrile purification process. A high-purity finished product may be obtained by performing operations of oxidation, rectification adsorption, drying, reflux rectification and filtration on industrial acetonitrile and controlling related parameters such as temperature, flow and the like, continuous production is ensured, a light transmittance of the finished product in ultraviolet rays of 200 to 260 nm is greater than or equal to 95%, water and impurities in the industrial acetonitrile are removed, and the requirements of the ultrahigh performance liquid chromatography-mass spectrometer are met; moreover, by controlling process parameters and equipment.

9 Claims, 17 Drawing Sheets

ACETONITRILE PURIFICATION PROCESS FOR ULTRAHIGH PERFORMANCE LIQUID CHROMATOGRAPHY-MASS SPECTROMETER

TECHNICAL FIELD

The present invention relates to the technical field of acetonitrile refining, and in particular, to an improved acetonitrile purification process for an ultrahigh performance liquid chromatography-mass spectrometer.

BACKGROUND

The ultrahigh performance liquid chromatography-mass spectrometer (UPLC-MS) reagent generally refers to a chromatographic special solvent or reagent, has high ultraviolet transmittance at the low wavelength position, and has strict and harsh requirements on indexes such as acidity, alkalinity, evaporation residues, metal ions, water and the like, some of which are required to reach ppb grade, even some of which are required to reach ppt grade. The UPLC-MS reagent refers to a standard reagent used during ultrahigh performance liquid chromatography-mass spectrometry. Under the chromatogaphic condition, only the peaks of specified compounds appear, the peaks of impurities cannot appear, or the peak of background noise is required to be lower than the sensitivity of the instrument. The UPLC-MS reagent has high purity, and has high requirements on dust, water and metal ions in addition to, the requirement on high content, thus belonging to the category of high-purity reagents. The UPLC-MS acetonitrile reagent is one of the commonly used liquid chromatography mobile phases. Its chromatographic pure market in China is mostly monopolized by foreign reagent companies, such as Merck, Sigma, Fisher, Tedia, etc., their products are expensive, which will lead to excessive cost consumption relative to the chromatographic pure users.

At present, a variety of acetonitrile purification processes have been reported at home and abroad. The main purification method includes: oxidation, dehydrogenation, heavy component removal, adsorption and rectification, or combination of oxidation, dehydrogenation, heavy component removal, decoloratiom/adsorption-rectification, and has the disadvantages of low yield, or low purity resulting high cost, or no capability of meeting the scientific research requirements on the indexes such as water, evaporation residues, metal ions, fluorescence, etc. Therefore, reducing the production cost and improving the quality of the UPLC-MS acetonitrile reagent need to be further explored and improved, Moreover, in the acetonitrile purification process, the adsorption column is generally used for the adsorption operation. To reduce the cost, it is necessary to regenerate the adsorption column. The adsorption column regeneration process is tedious, the operation intensity of people is high and a certain amount of waste water will be produced, which will have a certain influence on environmental protection.

SUMMARY

To solve the above problem, a first aspect of the present invention provides an improved acetonitrile purification process, including the following steps:

(1) adding an oxidizing agent into industrial acetonitrile containing impurities, water and acetonitrile to perform oxidation reaction, feeding the product into an adsorption and rectification tower for adsorption, and condensing the obtained tower top product of the adsorption and rectification tower to obtain a crude product, wherein a height of the adsorption and rectification tower is 7 to 30 m, and a pressure difference between the tower top and the tower bottom is 30 to 40 kPa;

(2) adding a drying, agent into the crude product for drying, heating and entering a reflux rectifying tower for total reflux after removing water, removing heavy component impurities at the tower bottom of the reflux rectifying tower, extracting and condensing light component impurities and acetonitrile at the tower top of the reflux rectifying tower to obtain a semi-finished product; and (3) removing 20 to 40 kg of semi-finished products extracted initially so as to remove the light component impurities, and filtering, the semi-finished product extracted later to obtain a finished product, wherein a light transmittance of the finished product in ultraviolet rays of 200 to 260 nm is greater than or equal to 95%.

As a preferred technical solution of the present invention, in the oxidation reaction, the temperature is 80 to 90° C., the time is 1 to 6 h, and the pressure is 10 to 90 KPa.

As a preferred technical solution of the present invention, the number of the adsorption and rectification tower is selected from one of one, two and three.

As a preferred technical solution of the present invention, the adsorption and rectification tower are filled with an adsorbent, and a screen size of the adsorbent is 5 to 6 mm.

As a preferred technical solution of the present invention, the flow of the total reflux is 10 to 100 kg/h, and the time is 2 to 10 h.

As a preferred technical solution of the present invention, the extracted flow is 10 to 30 kg/h, and the reflux ratio is (1-2):1.

As a preferred technical solution of the present invention, a filter membrane of the filtration includes a macromolecular filter membrane and an ion exchange filter membrane.

As a preferred technical solution of the present invention, the ion exchange filter membrane includes an anion exchange filter membrane and a cation exchange filter membrane.

As a preferred technical solution of the present invention, in the step (3), 20 to 40 kg of semi-finished products extracted initially are removed so as to remove the light component impurities, and the semi-finished products extracted later are sequentially filtered by the macromolecular filter membrane with a pore diameter of 150 to 250 nm, the ion exchange filter membrane and the macromolecular filter membrane with a pore diameter of 5 to 8 nm to obtain the finished product.

A second aspect of the present invention provides application of the improved acetonitrile purification process, which is applied to an ultrahigh performance liquid chromatography-mass spectrometer.

A main objective of the present invention is to provide an acetonitrile purification process. A high-purity finished product may be obtained by performing operations of oxidation, rectification adsorption, drying, reflux rectification and filtration on industrial acetonitrile and controlling related parameters such as temperature, flow and the like, continuous production is ensured, a light transmittance of the finished product in ultraviolet rays of 200 to 260 nm is greater than or equal to 95%, water and impurities in the industrial acetonitrile are removed, and the requirements of the ultrahigh liquid chromatography-mass spectrometer are met;

another objective of the present invention is to increase the yield of the finished products to above 95% and improve the purification efficiency by controlling process parameters and equipment; and another objective of the present invention is to replace the adsorption column by the adsorption and rectification tower, thus improving the regeneration efficiency and reducing environmental pollution while improving the purity.

Other objectives, advantages and novel characteristics of the present invention will be partially illustrated in the following description, and will partially become obvious to those skilled in the art after studying the following, or may be learned through the practice of the present invention. The objective and advantages of the present invention may be implemented and achieved by virtue of the means and combinations particularly pointed out in the appended claims.

Figure 1:
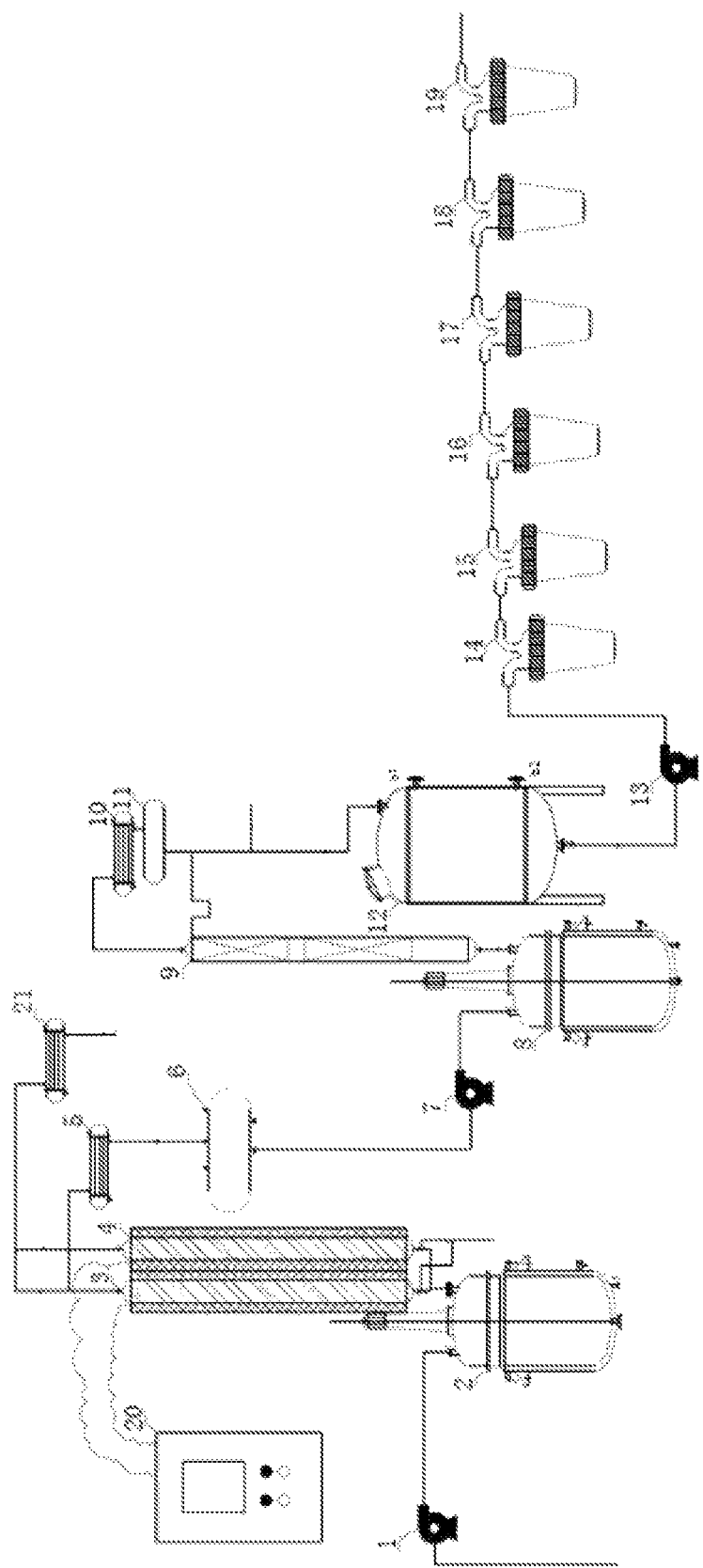
FIG. 1 is a process flowchart of an implementation manner in the improved acetonitrile purification process.

In the drawings, 1—raw material pump, 2—reaction kettle, 3—adsorption and rectification tower I, 4—adsorption and rectification tower II, 5—condenser I, 6—buffer tank, 7—feeding pump, 8—rectifying kettle, 9—reflux rectifying tower, 10—reflux condenser, 11—reflux tank, 12—finished product tank, 13—finished product pump, 14—macromolecular filter membrane filter I, 15—cation exchange filter membrane filter I, 16—cation exchange filter membrane filter H, 17—anion exchange filter membrane filter I, 18—anion exchange filter membrane filter H, 19—macromolecular filter membrane filter II, 20—controller, 21—regenerative condenser.

DESCRIPTION OF THE EMBODIMENTS

The contents of the present invention may be understood more easily with reference to the following detailed description of the preferred implementation methods of the present invention and the included embodiments. Unless otherwise defined, all technical and scientific terms used herein have the same meanings as those generally understood by a person of ordinary skill in the art to which the present invention belongs. In case of contradiction, the definition in this specification shall prevail.

The terms "including", "comprising", "having", "containing" or any other variations thereof used herein are intended to cover non-exclusive inclusion. For example, a composition, step, method, product or device including the listed elements are unnecessarily only limited to those elements, and may include other elements that are not explicitly listed, or elements inherent to the composition, step, method, product or device.

When equivalent, concentration, or other values or parameters are expressed in a range, a preferred range, or a range defined by a series of upper and lower limit preferred values, this should be understood as specifically disclosing all ranges formed by any pair of upper limit or preferred values in any range and lower limit or preferred values in any range, regardless of whether the range is separately disclosed. For example, when the range "1 to 5" is disclosed, the described range should be interpreted as including the ranges "1 to 4", "1 to 3", "1 to 2", "1 to 2 and 4 to 5", "1 to 3 and 5", etc. When a numerical value is described herein, unless otherwise specified, the range is intended to include its end value and all integers and fractions within the range.

The singular form includes a plural discussion object, unless the context clearly indicates otherwise. "Optional" or "any one" means that items or events described below may or may not occur, and the description includes the situation where the event occurs and the situation where the event does not occur.

Approximate terms in the description and the claims is used to modify a quantity, indicating that the present invention is not limited to the specific quantity, and may include modified parts that are close to the quantity, acceptable, and do not lead to change of related basic functions. Accordingly, the use of "about" or the like modifying a numerical value means that the present invention is not limited to the precise numerical value. In some examples, the approximate term may correspond to the accuracy of an instrument that measures a value. In the description and the claims of the present application, the range limitations may be combined and/or interchanged, and unless otherwise specified, these ranges include all subranges included therein.

In addition, the indefinite articles "a" and "an" before an element or component of the present invention have no limitation on the quantity requirements (that is, the occurrence number) of the element or component. Therefore, "a" or "an" should be interpreted as including one or at least one, and the element or component in the singular form also includes the plural form, unless the quantity is obviously intended to refer to the singular form.

The present invention will be described below by specific embodiments, but not limited to the specific embodiments given below.

To achieve the above objectives of the present invention, a first aspect of the present invention provides an improved acetonitrile purification process, including the following steps:

(1) adding an oxidizing agent into industrial acetonitrile containing impurities, water and acetonitrile to perform oxidation reaction, feeding the product into an adsorption and rectification tower for adsorption, and condensing the obtained tower top product of the adsorption and rectification tower to obtain a crude product, wherein a height of the adsorption and rectification tower is 7 to 30 m, and a pressure difference between the tower top and the tower bottom is 30 to 40 kPa;

(2) a drying agent was added into the crude product for drying, heating was conducted to enter a reflux rectifying tower for total reflux after removing water, heavy component impurities at the tower bottom of the reflux rectifying tower were removed, light component impurities and acetonitrile at the tower top of the reflux rectifying tower were extracted and condensed to obtain a semi-finished product; and (3) 20 to 40 kg of semi-finished products extracted initially were removed so as to remove the light component impurities, and the semi-finished product extracted later was filtered to obtain a finished product, wherein a light transmittance of the finished product in ultraviolet rays of 200 to 260 nm is greater than or equal to 95%.

The term "industrial acetonitrile" is a product prepared from acetonitrile-containing waste water of an acrylonitrile device through fractionation and refining. The acetonitrile is colorless transparent liquid, which is very easy to volatilize and has an odor similar to ether. The acetonitrile has excellent solvent performance and can dissolve a variety of organic, inorganic and gas substances. The acetonitrile has a certain toxicity, is infinitely mutually soluble with water and alcohol, can produce typical nitrile reaction, is used to prepare various typical nitrogen-containing compounds, and is an important organic intermediate, wherein the industrial acetonitrile meets SH/T 1627.1-2014.

The term "impurity" refers to other substances other than water and acetonitrile in the industrial acetonitrile. The acetonitrile may serve as a mobile phase and other excellent stationary phases of high-performance liquid chromatography, and has more stringent requirements on the contents of impurities. In addition to water, the impurities include hydrocyanic acid, acrylonitrile, cis-butene nitrile, trans-butene nitrile, allyl alcohol, oxazole, etc., which are required to be below a lower standard. These impurities will generate ultraviolet absorption in the ultraviolet absorption spectrum of 190-300 nm, so the purity of the acetonitrile may be judged by the ultraviolet absorption spectrum.

The term "light component impurity" refers to impurities with the boiling point less than that of the acetonitrile or the acetonitrile-water azeotrope in the rectification operation.

The term "heavy component impurity" refers to impurities with the boiling point higher than that of the acetonitrile or the acetonitrile-water azeotrope in the rectification operation.

The term "light transmittance" used above is defined as follows: the light transmittance indicates the ability of light passing through a medium and is the percentage of luminous flux passing through a transparent or semi-transparent object and the incident luminous flux. When the intensity I0 of the incident light is constant, the higher the intensity Ia of the medium absorbing light is, the lower the intensity It of the transmitted light. The ability of light passing, through the medium is represented by It/I0, which is called the light transmittance, represented by T, that is, T=It/I0, wherein the logarithm of the reciprocal of the light transmittance serves as absorbance, represented by A, that is, A=Ig(1/T)=Ig(I0/It).

Step (1)

In a preferred implementation solution of the present invention, the oxidizing agent accounts for 0.01-5 wt % of the industrial acetonitrile; further, the oxidizing agent of the present invention accounts for 0.1-1 wt % of the industrial acetonitrile; and further, the oxidizing agent of the present invention accounts for 0.1 wt % of the industrial acetonitrile.

In a preferred implementation solution of the present invention, in the oxidation reaction, the temperature is 80 to 90° C., the time is 1 to 6 h, and the pressure is 10 to 90 KPa.

According to the present invention, the oxidizing agent is not specifically limited, for example, potassium dichromate, potassium permanganate; organic peracid, such as peracetic acid, trifluoro peracetic acid, per benzoic acid and the like; chromium trioxide and chromic acid; lead tetraacetate, mercury acid and mercury acetate; selenium dioxide; sodium metaperiodate; osmium tetroxide; ruthenium tetroxide and sodium metaperiodate; ruthenium dioxide; alkali metal hypochlorite and alkali earth metal hypochlorite; a compound of superoxide and alkali, such as a compound of potassium superoxide and alkali, wherein the alkali may be potassium hydroxide, sodium hydroxide and lithium hydroxide; and a mixture of the above substances. In a preferred implementation solution of the present invention, the oxidizing agent is a mixture of potassium superoxide, potassium hydroxide and sodium hydroxide with a weight ratio of 1:(4-6):(6-10).

Since the industrial acetonitrile contains many impurities with the similar polarity to the acetonitrile, which are difficult to be removed directly through selective adsorption or rectification, the applicant firstly utilized the strong oxidizing property of the catalyst to oxidize the impurities in the industrial acetonitrile into polar oxygen-containing impurities with high boiling point or substances with great, polarity difference from the acetonitrile. The applicant found that when the compound of the potassium superoxide and alkali serves as the oxidizing agent and the content of the oxidizing agent and the conditions such as reaction time, temperature, pressure and the like are controlled, the impurities may be oxidized to generate substances with, great polarity difference from the acetonitrile, thereby facilitating further adsorption and rectification. Moreover, the applicant found that compared with the use of the potassium permanganate, the use of the compound of the potassium superoxide and alkali may achieve good oxidation effect under the condition of low oxidizing agent content and avoid the influence on the yield and purity due to too many byproducts caused by the potassium permanganate.

In a preferred implementation solution of the present invention, the number of the adsorption and rectification towers is selected from one, two and three; further, the number of the adsorption and rectification towers is two: further, the two adsorption and rectification towers are connected in parallel; and further, the adsorption and rectification towers are connected to a controller.

The term "controller" refers to a device that controls the flow velocity, temperature and pressure of regeneration of the adsorption and rectification towers so as to realize automatic regeneration.

In a preferred implementation solution of the present invention, the adsorption and rectification tower is filled with an adsorbent, and a screen size of the adsorbent is 5 to 6 mm.

The term "adsorbent" is used to remove impurities oxidized by the oxidizing agent and other impurities in the oxidation process. For example, the activated carbon removes polymers and aromatic substances. Aluminum oxide, silicon dioxide, a molecular sieve and aluminosilicate can trap polar organic compounds, such as amides and alcohol, and act as a dehydrating agent.

The adsorbent suitable for the present invention is selected from activated carbon, macroporous zeolite, aluminum oxide, silicon dioxide, aluminosilicate and a similar material for selectively adsorbing polar substances in the process, for example, macroporous polymer resin, and a molecular sieve known in the process for selectively removing water from the organic matter, such as a 3A or 4A molecular sieve. These materials may be filled in the adsorption and rectification tower to remove impurities. In a preferred implementation solution of the present invention, the adsorbent is the activated carbon; further, the screen size of the activated carbon is 5 to 6 mm; further, the screen size of the activated carbon is 5 mm; and further, the activated carbon is purchased from Shanghai Bilang Environmental Protection Technology Co., Ltd. (the screen size is 5 mm).

The term "screen size" used above is defined as follows: the screen size is a size of a screen which granules may pass through, and has a certain conversion relationship with the mesh number which refers to the density of the screen.

In the acetonitrile purification process, the adsorption column is often used to adsorb impurities, but the adsorption column regeneration process is tedious, the operation intensity of people is high and a certain amount of waste water will be produced, which will have a certain influence on environmental protection. The applicant added the adsorption and rectification tower in the oxidation operation, filled the rectifying tower with fillers and controlled the height and pressure difference of the rectifying tower, such that pollution of waste water may be reduced and the process operation may be simplified on the basis of further improving the purity. This is because when two parallel adsorption and rectification towers are used and are connected to the controller for acetonitrile purification, one adsorption and rectification tower performs adsorption and rectification and may be replaced by the other adsorption and rectification tower for acetonitrile purification after performing rectification for a period of time, and this adsorption and rectification tower is regenerated, thus ensuring the production continuity and improving the production efficiency.

Furthermore, in the regeneration process, the applicant found that through control of the controller, nitrogen is introduced from the tower bottom of the adsorption and rectification tower by controlling the flow velocity to be 10-20 m/s and the temperature to be 100-200° C. for regeneration, waste liquid is collected until no new waste liquid is generated, and the nitrogen continues to purge for 2 h to complete regeneration, such that artificial regeneration operation may be reduced through the control of the controller; and the waste liquid is heated, condensed and collected by the adsorption and rectification tower, such that the process of washing the adsorption column with water and the production of waste water may be reduced, thereby avoiding environmental pollution.

In addition, the applicant found that it is necessary to control the height and flow velocity of the adsorption and rectification tower and the size of the activated carbon, such that the pressure difference of the tower is 30-40 kPa. At this time, the light component impurities and a trace amount of heavy components in the gas phase from the oxidation reaction kettle are refluxed under the tower pressure, such that the purity is further improved and the efficiency is not reduced. When the pressure difference of the tower is fluffier increased due to small size of the activated carbon or large height of the tower, part of the acetonitrile will reflux to affect the purification efficiency. When the height of the tower is small or the size of the activated carbon is large, distillation and adsorption cannot be completely conducted so as to affect the purity of the final product.

Step (2)

In a preferred implementation solution of the present invention, the drying agent accounts for 0.01-5 wt % of the industrial acetonitrile; further, the drying agent accounts for 0.1-1 wt % of the industrial acetonitrile; and further, the drying agent accounts for 0.4 wt % of the industrial acetonitrile.

The drying agent is used to remove water in the industrial acetonitrile. The adsorbent suitable for the present invention is the well-known drying agent in the field, for example, silica gel, anhydrous calcium sulfate, calcium hydride, calcium chloride, phosphorus pentoxide, or combination of the above drying agents.

In a preferred implementation solution of the present invention, in the step (2), a drying agent was added into a crude product was added for drying, and after water was removed, the crude product was heated to 80-90° C. to enter the reflux rectifying tower for total reflux.

The term "total reflux" generally refers to an operation state of the rectification process. In the operation of the rectifying tower, steam goes upwards and liquid flows downwards, and the two phases are contact at each stage of tower plate or fillers of a tower middle section and transfer mass and heat. For continuous operation, the tower kettle needs to heat liquid to change the liquid into continuous steam, and the tower top needs to condense the steam into liquid. Under the general operation state, part of condensate at the tower top is extracted as distillate, and the other part of condensate refluxes to drip from the tower top, wherein the ratio of the reflux part to the extracted part is also called as a reflux ratio (R). In special cases, all the condensate at the tower top may reflux into the tower, that is, the reflux ratio R is equal to infinity. The operation state is called as total reflux. Generally, in the so-called total reflux, no product is extracted from the tower top, feeding and products at the tower bottom are zero, and the whole rectifying tower only exchanges heat with the outside world. It is worth noting that although no product is actually extracted in the total reflux operation, the state is convenient to control stably; moreover, the separation effect of the rectifying tower is improved along with the increase of the reflux ratio, and the total reflux corresponds to the theoretically optimal separation effect. Therefore, the total reflux operation is often used in the start-up debugging state of the rectifying tower and in the experimental study on the rectification process. During the start-up operation of the rectifying tower, the concentration of the materials at the tower top and the tower kettle do not meet the process requirements, so the materials cannot be extracted and sent to the next process. Through total reflux operation, concentration distribution may be established in the tower as soon as possible, such that the concentration of the materials at the tower top and the tower kettle meet the quality requirement in the shortest time; and the total reflux is relieved, the materials are added and the heating steam quantity is adjusted, such that smooth transition to normal production is facilitated.

In a preferred implementation solution of the present invention, the flow of the total reflux is 10 to 100 kg/h, and the time is 2 to 10 h.

The term "flow" used above is defined as follows: a mass flow, which refers the mass of fluid passing through the effective section of the closed pipeline or the open groove within per unit time.

In a preferred implementation solution of the present invention, the extracted flow is 10 to 30 kg/h, and the reflux ratio is (1-2):1.

The term "reflux ratio" used above is defined as follows: a ratio of the flow L of the reflux fluid returning, to the tower from the top of the distillation tower to the flow D of the product at the tower top during rectification operation, that is, R=L/D. The reflux ratio has an important influence on the separation effect and the economy of the rectification process.

The applicant found that the crude product after passing through the adsorption and rectification tower further includes part of water and impurities. To further improve the purity of the acetonitrile, the applicant adopted the drying agent to dry and remove water and then sent the acetonitrile into the reflux rectifying tower for total reflux. Moreover, the applicant found that it is necessary to control the flow of the total reflux to enhance the separation effect of the reflux rectifying tower and adjust the concentration and the content of the products at the tower top and the tower bottom, such that the heavy component impurities are concentrated at the tower bottom and the light component impurities are concentrated at the tower top. In this way, when the product at the tower top is extracted, the heavy component impurities may be avoided. Furthermore, the applicant found that all the light component impurities may be concentrated in 20-40 kg of semi-finished products extracted initially by controlling the extracted flow and the reflux ratio, such that the light component impurities may be removed by removing 20-40 kg of semi-finished products extracted initially, thus finally improving the purity of the finished product.

Furthermore, the applicant found that it is necessary to control the reflux flow and time to improve the separation effect of the reflux rectifying tower. When the reflux flow is too large or the time is too short, the separation effect is reduced. It is necessary to remove more semi-finished products, even heavy component impurities are brought. In addition, the extracted reflux ratio and the flow play an important role in removing the light components and the heavy components. Only when the extracted reflux ratio is (1-2):1 and the flow is 10-30 kg/h, the light component impurities and the heavy component impurities may be efficiently removed, and the purity and the purification efficiency may be improved.

Step (3)

In the filtration of the present invention, a filter membrane is adopted. The filter membrane suitable for the filtration of the present invention includes a macromolecular filter membrane and an ion exchange filter membrane.

The term "macromolecular filter membrane" is a semi-permeable film with a selective permeation function and made of a macromolecular material. By adoption of the semi-permeable film, a gas mixture, a liquid mixture or solutions of organic substances and inorganic substances are separated by taking pressure difference, temperature gradient, concentration gradient or potential difference as power, and the characteristics of energy saving, high efficiency, cleanness and the like are achieved. For example, the filter membrane may be a cellulose (CA\CN\CN-CA) filter membrane, a regenerated cellulose (RC) filter membrane, a nylon-6 filter membrane, a nylon-66 filter membrane, a polysulfone (PS) filter membrane, a polyether sulfone (PES) filter membrane, a polyvinylidene fluoride (PVDF) filter membrane, a polytetrafluoroethylene (PTFE) filter membrane, a polypropylene (PP) filter membrane and a high-density polyethylene (HDPE) filter membrane. In a preferred implementation solution of the present invention, the macromolecular filter membrane is a polytetrafluoroethylene filter membrane; and further, the polytetrafluoroethylene filter membrane is purchased from Shanghai Bitai Biotechnology Co. Ltd.

The polytetrafluoroethylene filter membrane is completely made of a natural and permanently hydrophobic PTFE material. Even if under very low-pressure difference, the polytetrafluoroethylene filter membrane can ensure the passage of moist air or other gases, but an aqueous solution cannot pass through the polytetrafluoroethylene filter membrane. The property of the polytetrafluoroethylene filter membrane is just opposite to that of a hydrophilic film. The PTFE filter membrane has extremely high chemical compatibility and almost can filter all organic solvents and strong corrosive chemicals.

In a preferred implementation solution of the present invention, in the step (3), 20 to 40 kg of semi-finished products extracted initially are removed so as to remove the light component impurities, and the semi-finished products extracted later are sequentially filtered by the macromolecular filter membrane with a pore diameter of 150 to 250 nm, the ion exchange filter membrane and the macromolecular filter membrane with a pore diameter of 5 to 8 nm to obtain the finished product.

The term "pore diameter" used above is defined as follows; a shape and a size of a pore channel in porous solid. The pore is actually very irregular. The pore is generally regarded as a circle, and the size of the pore is represented by the radius of the pore. The pore diameter distribution is often related to the adsorption capability of the adsorbent and the activity of the catalyst.

The applicant found that water and impurities are almost removed from the semi-finished product which is obtain through operation of oxidizing, adsorbing and rectifying, drying and rectifying the industrial acetonitrile, but a trace amount of impurities affect the final purity. The applicant may further remove the trace impurities through filtration by a proper macromolecular filter membrane and an ion exchange filter membrane. Furthermore, the applicant found that the trace impurities may be removed more efficiently when sequentially passing through the macromolecular filter membrane with a large screen size, the ion exchange filter membrane with a large screen size and the macromolecular filter membrane with a small screen size compared with firstly passing through the ion exchange filter membrane. This may be because the macromolecular filter membrane with the large screen size intercepts the large trace impurities and reduces the blockage and damage of the ion exchange filter membrane.

The term "ion exchange filter membrane" is a macromolecular membrane containing ionic groups and with selective permeability on ions in the solution. According to different functions and structures, the ion exchange film may be divided into five types: a cation exchange filter membrane, an anion exchange filter membrane, an amphoteric exchange filter membrane, a mosaic ion exchange filter membrane and a polyelectrolyte complex filter membrane. The ion exchange filter membrane suitable for the present invention is selected from a cation exchange filter membrane and an anion exchange filter membrane.

In a preferred implementation solution of the present invention, the ion exchange filter membrane includes a cation exchange filter membrane and an anion exchange filter membrane.

The term "cation exchange filter membrane" is a membrane with selectivity to cations, and has fixed groups and dissociable ions, for example, the sodium sulfonic acid type fixed group is, sulfonate, and dissociated ions are sodium ions. The cation exchange membrane may be regarded as a macromolecular electrolyte. Since the cation membrane is negatively charged, the original dissociated positive ions are dissociated into water under the action of water molecules, but the positively charged cations may pass through the cation membrane after electrification outside the membrane through the effect of an electric field, and the anions cannot pass through due to homopolar repulsion, so the cation exchange membrane has selective permeability. The active groups of the cationic filter membrane mainly include a sulfonic acid group, a carboxyl group, a phosphate group, a phosphorus acid group, a phenolic group, an arsenic acid group and a selenic acid group, wherein the sulfonic acid membrane is a strong acid type ion exchange membrane, and others are of weak acid type.

The cation exchange filter membrane suitable for the present invention is selected from a polytetrafluoroethylene sulfonated cationic filter membrane, a polysulfone sulfonated cationic filter membrane, a high-density polyethylene sulfonated cationic filter membrane, a polyether sulfone sulfonated cationic filter membrane, a polyvinyl alcohol sulfonated cationic filter membrane and a polytetrafluoroethylene carboxylic cationic filter membrane, or combination of the above cation exchange filter membranes; in a preferred implementation manner, the cationic filter membrane is the polytetrafluoroethylene sulfonated cationic filter membrane; and further, the polytetrafluoroethylene sulfonated cationic filter membrane of the present invention is purchased from Hangzhou Aier Environmental Protection Technology Co., Ltd.

The term "anionic filter membrane" is a kind of macromolecular polymer membrane containing alkaline active groups and with high selective permeability to anions, also known as an ion selective permeability membrane. The anionic filter membrane consists of three parts: a polymer main chain with a fixed group, i.e., a macromolecular matrix, (also called as a basement membrane), a positively charged active group (i.e., cation), and an anion capable of moving freely on the active group. The essence of the anion exchange membrane is an alkaline electrolyte with selective permeability to anions, so the anion exchange membrane is also called as an ion selective permeability membrane. Generally, cations such as —$NH^{3+}$, —$NR_2H^+$ or —$PR^{3+}$ serve as active exchange groups, and OH— generated at the cathode serves as a carrier and moves to an anode through the selective permeability of the anion exchange membrane.

The anion exchange filter membrane suitable for the present invention is selected from a polytetrafluoroethylene anionic filter membrane, a polysulfone anionic filter membrane, a polyethylene anionic filter membrane, a high-density polyether anionic filter membrane, a chitosan anionic filter membrane, or combination of the above anion exchange filter membranes; in a preferred implementation manner, the anion exchange filter membrane is the polytetrafluoroethylene anionic filter membrane; and further, the polytetrafluoroethylene anionic filter membrane is purchased from Hangzhou Aier Environmental Protection Technology Co., Ltd.

In a preferred implementation solution of the present invention, the number of the cation exchange filter membranes is as same as the number of the anion exchange filter membrane; and the number of the ion exchange filter membranes is selected from two, four and six. According to the present invention, the specific sequence of the semi-finished product passing through the cation exchange filter membrane and the anion exchange filter membrane is not, further specified.

In addition, the applicant found that the purification efficiency may be further improved by selecting appropriate filter membrane types, especially selecting polytetrafluoroethylene as a filter membrane of a base material, which may be because C—H bonds in the polytetrafluoroethylene are all replaced by C—F bonds. However, compared with hydrogen atoms the fluorine atoms have more electronic structures and high electronegativity, such that the polarity and the interaction force of the C—F bonds are reduced while the stability of the C—F bonds is improved, and it is more beneficial to block the passage of the trace impurities when the semi-finished product passes through the filter membrane of the polytetrafluoroethylene base material. In particular, when the anion and cation exchange membranes of the polytetrafluoroethylene are used, high stability and electronegativity of the C—F bonds enhance the ionic conductance of the filter membrane, thereby more efficiently filtering the impurities and preventing the polytetrafluoroethylene from bringing new impurities.

An implementation manner of acetonitrile purification will be described with reference to FIG. 1, but is not limited to the following implementation manners.

FIG. 1 shows a process flowchart of an acetonitrile purification process. Industrial acetonitrile passed through a raw material pump 1 and was conveyed to a reaction kettle 2, an oxidizing agent was added into the reaction kettle 2, and the reaction kettle was heated to 80-90° C. to react for 1-6 h by controlling the reaction pressure to be 10-90 kPa; after the reaction was completed, distillation and adsorption were started through an adsorption and rectification tower I 3 or an adsorption and rectification tower II 4 (in the adsorption and rectification tower I 3 and the adsorption and rectification tower II 4, one is for online adsorption and rectification and the other one is regenerated for future use, when the adsorption and rectification tower I 3 or the adsorption and rectification tower II 4 was regenerated, nitrogen was introduced from the bottom of the rectification tower I 3 or the adsorption and rectification tower II 4, the flow velocity was controlled to be 10-20 m/s by a controller 20, the temperature of the rectification tower I 3 or the adsorption and rectification tower II 4 was 100-200° C., condensation was conducted by a regenerative condenser 21, then waste liquid was collected until no waste liquid was in the regenerative condenser 21, and the nitrogen was used to continue to purge for 2 h to complete regeneration of the adsorption and rectification tower I 3 or the adsorption and rectification tower II 4), materials were fed into a buffer tank 6 after passing through a condenser I 5, after distillation, materials were fed into a rectifying kettle through a feeding pump 7, a drying agent was added into the rectifying kettle 8 after materials were fed into the rectifying kettle 8, the rectifying kettle 8 was heated to 80-90° C., the materials entered into a reflux rectifying tower 9 to perform rectification under normal pressure, the tower top of the reflux rectifying tower 9 communicated with a loop of a reflux condenser 10 and a reflux tank 11 to establish total reflux by controlling, the reflux flux to be 10-100 kg/h and the time of the total reflux to be 2-10 h, then extraction was started by controlling the extracted flow to be 10-30 kg/h and the reflux ratio to be (1-2):1, 20-40 kg of unqualified parts extracted at the beginning were removed, the remaining qualified part was extracted into a finished product tank 12 to, obtain a semi-finished product, the semi-finished product was conveyed by a finished product pump 13 to, be filtered sequentially by a macromolecular filter membrane filter I 14, a cation ion exchange filter membrane filter I 15, an anion exchange filter membrane filter II 16, an anion exchange filter membrane filter I 17, an anion exchange filter membrane filter II 18 and a macromolecular filter membrane filter II 19 to obtain a qualified finished product of UPLC-MS grade chromatographic acetonitrile, wherein the yield of the process reaches to more than 95%.

A material of a device for the acetonitrile purification process according to the present invention is selected from enamel, polytetrafluoroethylene, graphene, graphite and high-density polyethylene. For example, materials of the reaction kettle, the rectifying kettle, the reflux tank and the finished product tank may be the enamel, the high-density polyethylene and the like, and lining materials of the condenser, the reflux rectifying tower, the feeding pump and the finished product pump may be the enamel, the polytetrafluoroethylene, the graphene, the graphite, the high-density polyethylene and the like.

At present, most acetonitrile purification equipment is made of iron-containing materials such as carbon steel, stainless steel and the like. As the use time increases, it is prone to corrode to release metal ions such as iron ions, such that the metal ions such as iron are mixed into the acetonitrile and may react with the acetonitrile and impurities to affect the quality of the acetonitrile. The applicant may avoid the influence on the acetonitrile by the introduction of the metal ions by controlling materials of all devices of the present invention as the enamel, the polytetrafluoroethylene, the graphene, the graphite and the high-density polyethylene, thereby being beneficial to realizing large-scale production and ensuring the purity and yield of the final product.

According to the present invention, production is realized through the production sequence of oxidation, adsorption, rectification and filtration, and the production sequence cannot be changed at will. Firstly, the impurities are oxidized into substances with polarity greatly different from the acetonitrile before being selectively removed through adsorption and, rectification, and new impurities may be generated due to the adsorbent in the adsorption process, so the new impurities in the adsorption process are removed through rectification operation after adsorption. In addition, compared with the operations such as adsorption, the rectification is high in energy consumption. The target purity may be achieved through one-time rectification by performing adsorption before rectification and performing filtration after rectification, thus avoiding the problem of increased energy consumption caused by multiple rectifications. According to the present invention, production of the acetonitrile with the ultrahigh performance chromatography-mass spectrometry purity is finally realized by using a certain production sequence and controlling parameters therein. Moreover, according to the application, the conventional adsorption column is replaced by the adsorption and rectification tower, such that the pollution of manual operation and waste water in the regeneration process may be reduced, and environmental protection is enhanced while the operation is simplified.

A second aspect of the present invention provides application of the improved acetonitrile purification process described above, which is applied to an ultrahigh performance liquid chromatography-mass spectrometer.

EMBODIMENT

The present invention is described in detail through embodiments. It is essential to point out herein that the following embodiments are merely intended to further illustrate the present invention and are not construed as limitation to the scope of protection of the present invention, and that some non-essential modifications and adaptations made by those skilled in the art according to the above content of the present invention still fall within the scope of protection of the present invention.

Embodiment 1

The embodiment provides an improved acetonitrile purification process, including the following steps:
(1) an oxidizing agent which accounts for 0.01 wt % of industrial acetonitrile and is a mixture of potassium superoxide, potassium hydroxide and sodium hydroxide with a weight ratio of 1:5:8 was added into industrial acetonitrile containing impurities, water and acetonitrile, the materials were, fed into an adsorption and rectification tower for adsorption after oxidation reaction for 1 h at 80° C. and under the pressure of 10 KPa, the obtained tower top product of the adsorption and rectification tower was condensed to obtain a crude product, wherein a height of the adsorption and rectification tower is 7 m, a pressure difference of the tower top and the tower bottom is 30 kPa, there are two adsorption and rectification towers which are connected in parallel, the two adsorption and rectification towers are connected to a controller respectively, the adsorption and rectification towers are filled with adsorbents, and a screen size of the adsorbent is 5 mm;
(2) phosphorus pentoxide which accounts for 0.1 wt % of the industrial acetonitrile was added into the crude product, the industrial acetonitrile was heated to 80° C. after water removal to enter a reflux rectifying tower, total reflux was conducted at the flow of 10 kg/h for 2 h, heavy component impurities at the tower bottom of the reflux rectifying tower were removed, and light component impurities and acetonitrile at the tower top of the reflux rectifying tower were extracted and condensed under the conditions that the flow is 10 kg/h and the reflux ratio is 1:1 to obtain a semi-finished product; and
(3) 20 kg of semi-finished products initially extracted were removed so as to remove the light component impurities, and the semi-finished products extracted later were filtered sequentially by a polytetrafluoroethylene filter membrane with a pore diameter of 200 nm, a polytetrafluoroethylene sulfonated cationic filter membrane, a polytetrafluoroethylene sulfonated cationic filter membrane, a polytetrafluoroethylene anionic filter membrane, a polytetrafluoroethylene anionic filter membrane and a polytetrafluoroethylene filter membrane with a pore diameter of 7 nm to obtain a finished product.

The activated carbon is purchased from Shanghai Bilang Environmental Protection Technology Co., Ltd.

The polytetrafluoroethylene filter membrane is purchased from Shanghai Bitai Biotechnology Co., Ltd.

The polytetrafluoroethylene sulfonated cationic filter membrane is purchased from Hangzhou Aier Environmental Protection Technology Co., Ltd.

The polytetrafluoroethylene anionic filter membrane is purchased from Hangzhou Aier Environmental Protection Technology Co., Ltd.

Embodiment 2

The embodiment provides an improved acetonitrile purification process, including the following steps:
(1) an oxidizing agent which accounts for 1 wt % of industrial acetonitrile and is a mixture of potassium superoxide, potassium hydroxide and sodium hydroxide with a weight ratio of 1:5:8 was added into industrial acetonitrile containing impurities, water and acetonitrile, the materials were fed into an adsorption and rectification tower for adsorption after oxidation reaction for 6 h at 90° C. and under the pressure of 90 KPa, the obtained tower top product of the adsorption and rectification tower was condensed to obtain a crude product, wherein a height of the adsorption and rectification tower is 30 m, a pressure difference of the tower top and the tower bottom is 40 kPa, there are two adsorption and rectification towers which are connected in parallel, the two adsorption and rectification towers are connected to a controller respectively, the adsorption and rectification towers are filled with adsorbents, and a screen size of the adsorbent is 6 mm;
(2) phosphorus pentoxide which accounts for 1 wt % of the industrial acetonitrile was added into the crude product, the industrial acetonitrile was heated to 90° C. after water removal to enter a reflux rectifying tower, total reflux was conducted at the flow of 100 kg/h for 10 h, heavy component impurities at the tower bottom of the reflux rectifying tower were removed, and light component impurities and acetonitrile at the tower top of the reflux rectifying tower were extracted and condensed under the conditions that the flow is 30 kg/h and the reflux ratio is 2:1 to obtain a semi-finished product; and
(3) 40 kg of semi-finished products initially extracted were removed so as to remove the light component impurities, the semi-finished products extracted later were filtered sequentially by a polytetrafluoroethylene filter membrane with a pore diameter of 200 nm, a polytetrafluoroethylene sulfonated cationic filter membrane, a polytetrafluoroethylene sulfonated cationic filter membrane, a polytetrafluoroethylene anionic filter membrane, a polytetrafluoroethylene anionic filter membrane and a polytetrafluoroethylene filter membrane with a pore diameter of 7 nm to obtain a finished product.

The activated carbon is purchased from Shanghai Bilang Environmental Protection Technology Co., Ltd.

The polytetrafluoroethylene filter membrane is purchased from Shanghai Bitai Biotechnology Co., Ltd.

The polytetrafluoroethylene sulfonated cationic filter membrane is purchased from Hangzhou Aier Environmental Protection Technology Co., Ltd.

The polytetrafluoroethylene anionic filter membrane is purchased from Hangzhou Aier Environmental Protection Technology Co., Ltd.

Embodiment 3

The embodiment provides an improved acetonitrile purification process, including the following steps:
(1) an oxidizing agent which accounts for 0.1 wt % of industrial acetonitrile and is a mixture of potassium superoxide, potassium hydroxide and sodium hydroxide with a weight ratio of 1:5:8 was added into industrial acetonitrile containing impurities, water and acetonitrile, the materials were fed into an adsorption and rectification tower for adsorption after oxidation reaction for 4 h at 90° C. and under the pressure of 60 KPa, the obtained tower top product of the adsorption and rectification tower was condensed to obtain a crude product, wherein a height of the adsorption and rectification tower is 20 m, a pressure difference of the tower top and the tower bottom is 40 kPa, there are two adsorption and rectification towers which are connected in parallel, the two adsorption and rectification towers are connected to a controller respectively, the adsorption and rectification towers are filled with adsorbents, and a screen size of the adsorbent is 5 mm;
(2) phosphorus pentoxide which accounts for 0.4 wt % of the industrial acetonitrile was added into the crude product, the industrial acetonitrile was heated to 90° C. after water removal to enter a reflux rectifying tower, total reflux was conducted at the flow of 75 kg/h for 7 h, heavy component impurities at the tower bottom of the reflux rectifying tower were removed, and light component impurities and acetonitrile at the tower top of the reflux rectifying tower were extracted and condensed under the conditions that the flow is 20 kg/h and the reflux ratio is 1.5:1 to obtain a semi-finished product; and
(3) 30 kg of semi-finished products initially extracted were removed so as to remove the light component impurities, and the semi-finished products extracted later were filtered sequentially by a polytetrafluoroethylene filter membrane with a pore diameter of 200 nm, a polytetrafluoroethylene sulfonated cationic filter membrane, a polytetrafluoroethylene sulfonated cationic filter membrane, a polytetrafluoroethylene anionic filter membrane, a polytetrafluoroethylene anionic filter membrane and a polytetrafluoroethylene filter membrane with a pore diameter of 7 nm to obtain a finished product.

The activated carbon is purchased from Shanghai Bilang Environmental Protection Technology Co., Ltd.

The polytetrafluoroethylene filter membrane is purchased from Shanghai Bitai Biotechnology Co., Ltd.

The polytetrafluoroethylene sulfonated cationic filter membrane is purchased from Hangzhou Aier Environmental Protection Technology Co., Ltd.

The polytetrafluoroethylene anionic filter membrane is purchased from Hangzhou Aier Environmental Protection Technology Co., Ltd.

Embodiment 4

The embodiment provides an improved acetonitrile purification process. The specific implementation manner in this embodiment is as same as that in Embodiment 3, except that in the step (1), an oxidizing agent which accounts for 0.1 wt % of industrial acetonitrile and is a mixture of potassium superoxide, potassium hydroxide and sodium hydroxide with a weight ratio of 1:5:8 was added into industrial acetonitrile containing impurities, water and acetonitrile, the materials were fed into an adsorption and rectification tower for adsorption after oxidation reaction for 4 h at 90° C. and under the pressure of 60 KPa, the obtained tower top product of the adsorption and rectification tower was condensed to obtain a crude product, wherein a height of the adsorption and rectification tower is 20 m, a pressure difference of the tower top and the tower bottom is 15 kPa, there are two adsorption and rectification towers which are connected in parallel, the two adsorption and rectification towers are connected to a controller respectively, the adsorption and rectification towers are filled with adsorbents, and a screen size of the adsorbent is 5 mm.

Embodiment 5

The embodiment provides an improved acetonitrile purification process. The specific implementation manner in this embodiment is as same as that in Embodiment 3, except that in the step (1), an oxidizing agent which accounts for 0.1 wt % of industrial acetonitrile and is a mixture of potassium superoxide, potassium hydroxide and sodium hydroxide with a weight ratio of 1:5:8 was added into industrial acetonitrile containing impurities, water and acetonitrile, the materials were fed into an adsorption and rectification tower for adsorption after oxidation reaction for 4 h at 90° C. and under the pressure of 60 KPa, the obtained tower top product of the adsorption and rectification tower was condensed to obtain a crude product, wherein a height of the adsorption and rectification tower is 20 m, a pressure difference of the tower top and the tower bottom is 40 kPa, there are two adsorption and rectification towers which are connected in parallel, the two adsorption and rectification towers are connected to a controller respectively, the adsorption and rectification towers are filled with adsorbents, and a screen size of the adsorbent is 8 mm.

Embodiment 6

The embodiment provides an improved acetonitrile purification process. The specific implementation manner in this embodiment, is as same as that in Embodiment 3, except that in the step (2), phosphorus pentoxide which accounts for 0.4 wt % of the industrial acetonitrile was added into the crude product, the industrial acetonitrile was heated to 90° C. after water removal to enter a reflux rectifying tower, total reflux was conducted at the flow of 140 kg/h for 7 h, heavy component impurities at the tower bottom of the reflux rectifying tower were removed, and light component impurities and acetonitrile at the tower top of the reflux rectifying tower were extracted and condensed under the conditions that the flow is 20 kg/h and the reflux ratio is 1.5:1 to obtain a semi-finished product.

Embodiment 7

The embodiment provides an improved acetonitrile purification process. The specific implementation manner in this embodiment is as same as that in Embodiment 3, except that in the step (2), phosphorus pentoxide which accounts for 0.4 wt % of the industrial acetonitrile was added into the crude product, the industrial acetonitrile was heated to 90° C. after water removal to enter a reflux rectifying tower, total reflux was conducted at the flow of 75 kg/h for 1 h, heavy component impurities at the tower bottom of the reflux rectifying tower were removed, and light component impurities and acetonitrile at the tower top of the reflux rectifying tower were extracted and condensed under the conditions that the flow is 20 kg/h and the reflux ratio is 1.5:1 to obtain a semi-finished product.

Embodiment 8

The embodiment provides an improved acetonitrile purification process. The specific implementation manner in this embodiment is as same as that in Embodiment 3 except that in the step (2), phosphorus pentoxide which accounts for 0.4 wt % of the industrial acetonitrile was added into the crude product, the industrial acetonitrile was heated to 90° C. after water removal to enter a reflux rectifying tower, total reflux was conducted at the flow of 75 kg/h for 7 h, heavy component impurities at the tower bottom of the reflux rectifying tower were removed, and light component impurities and acetonitrile at the tower top of the reflux rectifying tower were extracted and condensed under the conditions that the flow is 40 kg/h and the reflux ratio is 1.5:1 to obtain a semi-finished product.

Embodiment 9

The embodiment provides an improved acetonitrile purification process. The specific implementation manner in this embodiment, is as same as that in Embodiment 3, except that in the step (3), the semi-finished products extracted later were filtered sequentially by a polytetrafluoroethylene filter membrane with a pore diameter of 200 nm, a polytetrafluoroethylene sulfonated cationic filter membrane, a polytetrafluoroethylene sulfonated cationic filter membrane, a polytetrafluoroethylene anionic filter membrane, a polytetrafluoroethylene anionic filter membrane and a polytetrafluoroethylene filter membrane with a pore diameter of 7 nm to obtain a finished product.

Embodiment 10

The embodiment provides an improved acetonitrile purification process. The specific implementation manner in this embodiment is as same as that in Embodiment 3, except that in the step (3), 60 kg of semi-finished products initially extracted were removed so as to remove the light component impurities, and the semi-finished products extracted later were filtered sequentially by a polytetrafluoroethylene filter membrane with a pore diameter of 200 nm, a polytetrafluoroethylene sulfonated cationic filter membrane, a polytetrafluoroethylene sulfonated cationic filter membrane, a polytetrafluoroethylene anionic filter membrane, a polytetrafluoroethylene anionic filter membrane and a polytetrafluoroethylene filter membrane with a pore diameter of 7 nm to obtain a finished product.

Embodiment 11

The embodiment provides an improved acetonitrile purification process. The specific implementation manner in this embodiment is as same as that in Embodiment 3, except that in the step (3), 30 kg of semi-finished products initially extracted were removed so as to remove the light component impurities, and the semi-finished products extracted later were filtered sequentially by a polypropylene filter membrane with a pore diameter of 200 nm, a polytetrafluoroethylene sulfonated cationic filter membrane, a polytetrafluoroethylene sulfonated cationic filter membrane, polytetrafluoroethylene anionic filter membrane, a polytetrafluoroethylene anionic filter membrane and a polypropylene, filter membrane with a pore diameter of 7 nm to obtain a finished product, wherein the polypropylene filter membrane is purchased from Shanghai Bitai Biotechnology Co., Ltd.

Embodiment 12

The embodiment provides an improved acetonitrile purification process. The specific implementation manner in this embodiment is as same as that in Embodiment 3, except that in the step (3), 30 kg of semi-finished products initially extracted were removed so as to remove the light component impurities, and the semi-finished products extracted later were filtered sequentially by a polytetrafluoroethylene filter membrane with a pore diameter of 200 nm, a polyether sulfone sulfonated cationic filter membrane, a polyether sulfone sulfonated cationic filter membrane, polytetrafluoroethylene anionic filter membrane, a polytetrafluoroethylene anionic filter membrane and a polypropylene filter membrane with a pore diameter of 7 nm to obtain a finished product, wherein the polyether sulfone sulfonated cationic filter membrane is purchased from Shanghai Bitai Biotechnology Co., Ltd.

Embodiment 13

The embodiment provides an improved acetonitrile purification process. The specific implementation manner in this embodiment is as same as that in Embodiment 3 except that in the step (3), 30 kg of semi-finished products initially extracted were removed so as to remove the light component impurities, and the semi-finished products extracted later were filtered sequentially by a polytetrafluoroethylene filter membrane with a pore diameter of 200 nm, a polytetrafluoroethylene sulfonated cationic filter membrane, a polytetrafluoroethylene sulfonated cationic filter membrane, a polysulfone anionic filter membrane, a polysulfone anionic filter membrane and a polypropylene filter membrane with a pore diameter of 7 nm to obtain a finished product, wherein the polysulfone anionic filter membrane is purchased from Shanghai Bitai Biotechnology Co., Ltd.

Performance Evaluation

The finished product prepared by the acetonitrile purification process provided by the embodiment serves as a sample to perform the following experiments.

1. Ultraviolet transmittance test: the sample provided by the embodiment was subjected to ultraviolet transmittance test of 190-260 nm., wherein the 190 nm ultraviolet transmittance≥10%, 195 nm ultraviolet transmittance≥80%, 200 nm ultraviolet transmittance≥95%, 210 nm ultraviolet transmittance≥96%, 220 nm ultraviolet transmittance≥97%, 230 nm ultraviolet transmittance≥98%, ultraviolet transmittance of ultraviolet wavelength being more than 240 nm≥99%. The results are shown in Table 1.

TABLE 1

| Performance characterization test | | | | | | | | |
|---|---|---|---|---|---|---|---|---|
| Embodiment | 195 nm | 200 nm | 210 nm | 220 nm | 230 nm | 240 nm | 250 nm | 260 nm |
| 1 | 88.5 | 96.7 | 97.9 | 98.8 | 99.3 | 99.6 | 99.5 | 99.5 |
| 2 | 90.8 | 97.3 | 97.9 | 99.1 | 99.4 | 99.7 | 99.7 | 99.8 |
| 3 | 92.3 | 98.1 | 98.6 | 99.4 | 99.6 | 99.8 | 99.8 | 99.6 |
| 4 | 83.6 | 94.3 | 95.7 | 96.1 | 97.2 | 98.2 | 98.5 | 98.5 |
| 5 | 76.9 | 93.4 | 95.7 | 95.6 | 96.2 | 98.1 | 97.5 | 98.1 |
| 6 | 78.1 | 89.3 | 92.2 | 93.1 | 94.8 | 96.5 | 97.9 | 98.1 |
| 7 | 73.4 | 88.6 | 90.2 | 93.7 | 94.8 | 96.5 | 96.8 | 97.1 |
| 8 | 75.1 | 88.2 | 92.3 | 92.9 | 95.4 | 96.3 | 97.5 | 98.9 |
| 9 | 70.5 | 87.4 | 88.2 | 90.1 | 89.9 | 95.8 | 95.2 | 95.8 |
| 10 | 92.2 | 98.2 | 98.5 | 99.3 | 99.6 | 99.8 | 99.8 | 99.7 |
| 11 | 76.2 | 92.1 | 94.5 | 95.4 | 97.9 | 98.5 | 98.7 | 98.5 |
| 12 | 73.9 | 89.2 | 92.3 | 94.1 | 95.7 | 97.4 | 97.9 | 98.2 |
| 13 | 74.5 | 90.3 | 92.9 | 95.2 | 97.3 | 98.1 | 97.8 | 98.4 |

2. Purity test: the purity of the sample provided by Embodiment 3 was tested, wherein the test standard of the acetonitrile for the ultrahigh performance liquid chromatography-mass spectrometry and the test result of the embodiment are shown in Table 2. It is found that the acetonitrile provided by Embodiment 3 meets the standard of the acetonitrile for the ultrahigh performance liquid chromatography-mass spectrometry. Moreover, the acetonitrile in Embodiments 1-2 was subjected to the above test, and it is also found that the acetonitrile meets the standard. The weight percentage of the acetonitrile for the ultrahigh performance liquid chromatography-mass spectrometer obtained in Embodiments 1-3 in industrial acetonitrile was calculated to serve as the yield of Embodiments 1-3, it is found that the yield is greater than 95%.

TABLE 2

| Performance characterization test | | |
|---|---|---|
| Detection Items | Standard Regulation | Measured value |
| Content | ≥99.9% | 99.999% |
| Acidity | ≤0.0002 meq/g | 0.00010 meq/g |
| Alkalinity | ≤0.0002 meq/g | 0.000025 meq/g |
| Boiling point | 80-->82 ° C. | 81 ° C. |
| Chromaticity | ≤10 APHA | 1 APHA |
| Evaporation residue | ≤2 ppm | 0.05 ppm |
| Water | ≤200 ppm | 52.1 ppm |
| Gradient (210 nm) | ≤0.5 mAU | 0.3 mAU |
| Gradient (254 nm) | ≤0.3 mAU | 0.05 mAU |
| Fluorescence (quinine) 254/365 nm | ≤0.5 ppb | 0.06 ppb |
| MS-ESI/APCI (as Reserpine negative) | ≤10 ppb | 3 ppb |

TABLE 2-continued

Performance characterization test

| Detection Items | Standard Regulation | Measured value |
|---|---|---|
| MS-ESI/APCI (as Reserpine positive) | ≤2 ppb | 0.7 ppb |
| Al | ≤5 ppb | 0.6 ppb |
| Ca | ≤5 ppb | 1 pb |
| Fe | ≤5 ppb | 0.2 ppb |
| K | ≤5 ppb | 2 ppb |
| Mg | ≤5 ppb | 0.9 ppb |
| Na | ≤25 ppb | 10 ppb |

Figure 2:
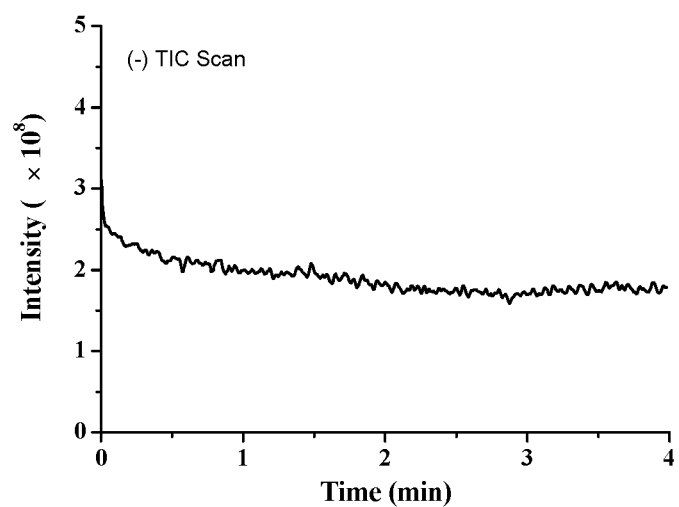
FIG. 2 is a TIC (ESI−) diagram of an acetonitrile finished product provided by Embodiment 3.
Figure 3:
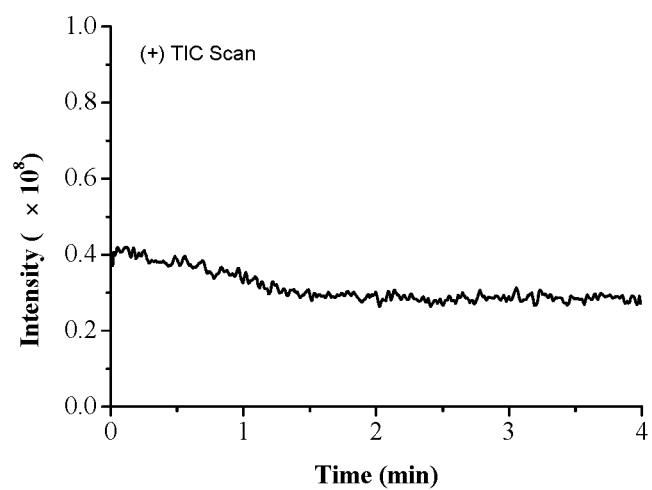
FIG. 3 is a TIC (ESI+) diagram of an acetonitrile finished product provided by Embodiment 3.

3. Baseline noise test: the sample provided by Embodiment 3 was subjected to LC-MS-MS baseline noise analysis:
   test instrument: LCMS-8045;
   chromatographic column: Shimpack VP-ODS, 2.0 mm*150 mm;
   ion source: ESI/APCI positive and negative mode;
   test method: data was acquired by taking pure acetonitrile as a mobile phase at a flow velocity of 0.5 mL/min and in a Scan mode to obtain diagrams of TIC(ESI−) and TIC (ESI+) respectively, shown in FIG. 2 and FIG. 3, wherein it can be seen from FIG. 2 and FIG. 3 that under the isocratic condition that the mobile phase is, pure acetonitrile, the acetonitrile finished product provided by the embodiment has a lower baseline noise value, which shows that the product has lower impurity content.

4. Mass spectrometry; the acetonitrile finished product provided by the embodiment and the LCMS grade and HPLC grade acetonitrile of Merck were subjected to mass spectrum test:
   test instrument: Waters TQD triple quadrupole mass spectrometer;
   test method: samples were directly introduced into mass spectrum (without passing through liquid phase), ESI+ and the Scan mode, and the acetonitrile provided by Embodiment 3 and the LCMS grade and HPLC grade acetonitrile of Merck were analyzed respectively:

(1) Comparison between the acetonitrile finished product provided by the present invention and the LCMS acetonitrile of Merck.

Figure 4:
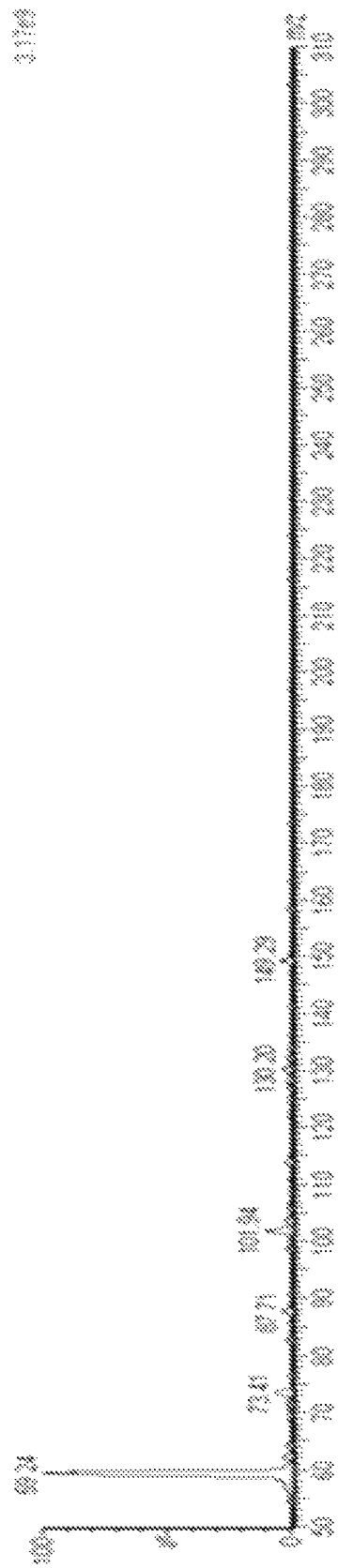
FIG. 4 is a mass spectrum of LCMS acetonitrile of a first batch of Merck.
Figure 5:
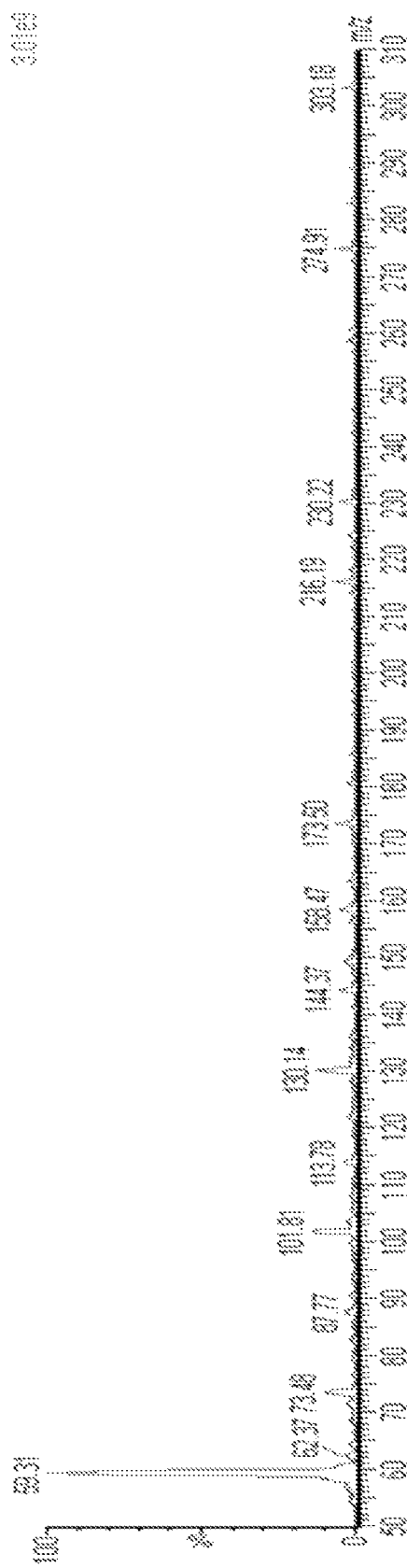
FIG. 5 is a mass spectrum of LCMS acetonitrile of a second batch of Merck.
Figure 6:
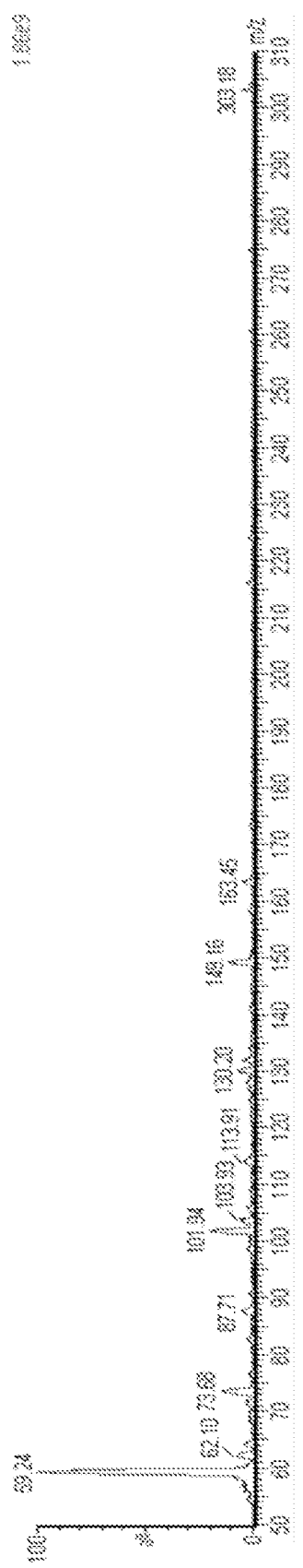
FIG. 6 is a mass spectrum of an acetonitrile finished product provided by Embodiment 3.

FIG. 4 to FIG. 6 are mass spectrograms of the first batch of LCMS acetonitrile of Merck, the second batch of LCMS acetonitrile of Merck and the acetonitrile finished product provided by Embodiment 3. Through overall comparison among FIG. 4 to FIG. 6, it is found that the m/z 59.2 ($CH_3CN^+NH^{4+}$) intensity is different in the acetonitrile finished product provided by Embodiment 3, and the values of the two batches of the LCMS acetonitrile of Merck are close to each other.

Figure 7:
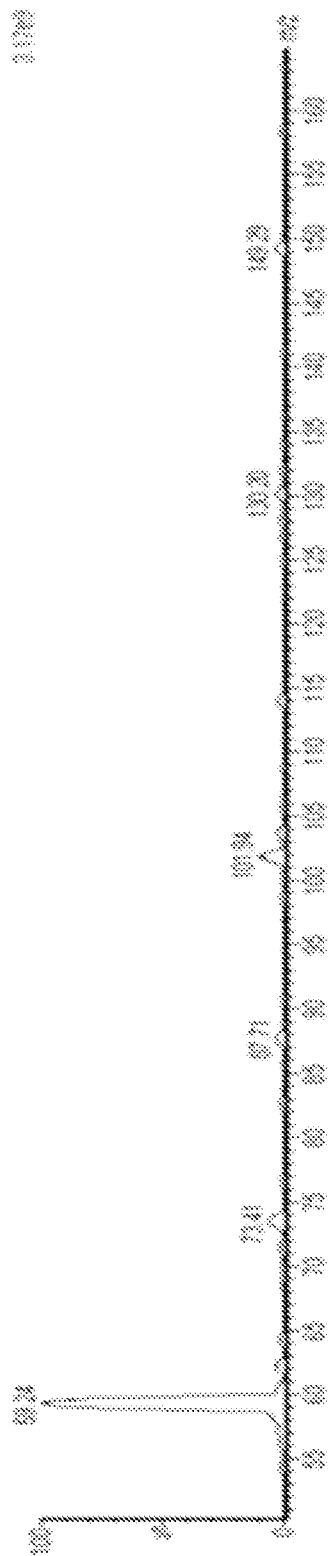
FIG. 7 is a partial enlarged view of m/z at an interval of 55-160 in FIG. 4.
Figure 8:
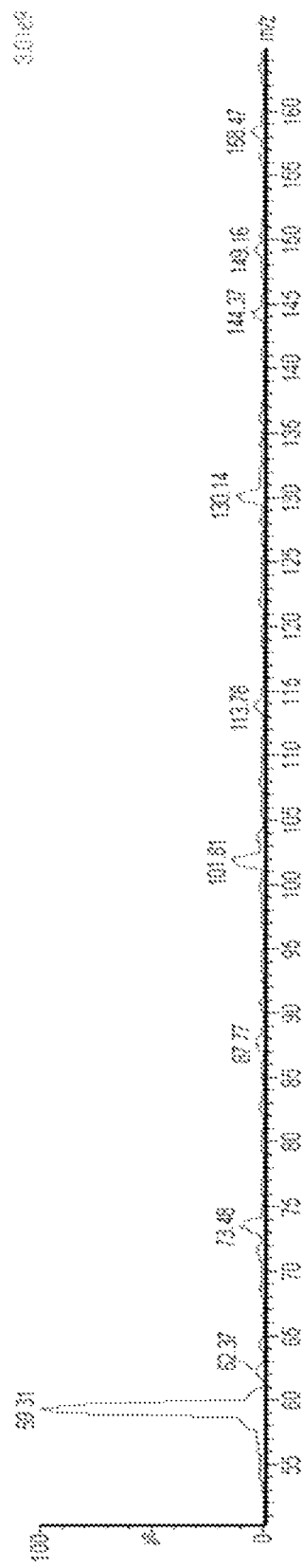
FIG. 8 is a partial enlarged view of m/z at an interval of 55-160 in FIG. 5.
Figure 9:
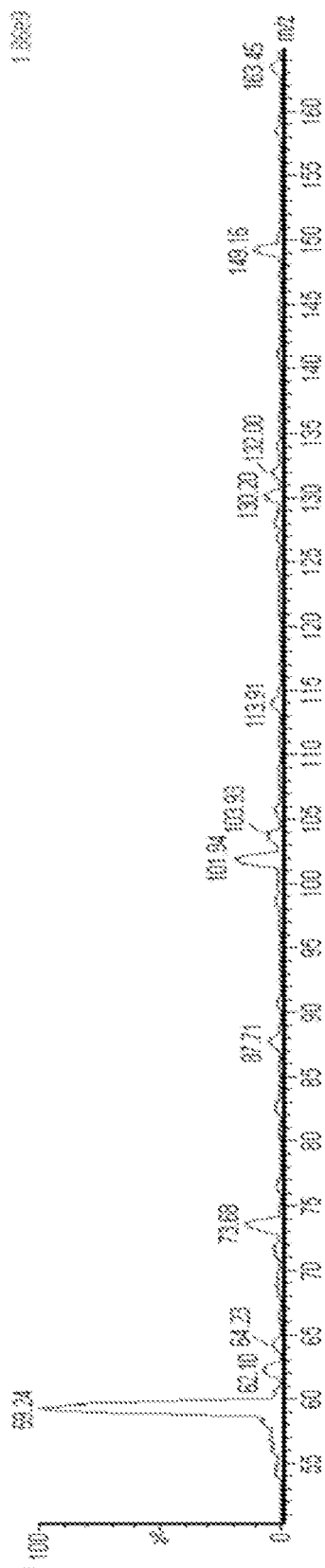
FIG. 9 is a partial enlarged view of m/z at an interval of 55-160 in FIG. 6.

The mass spectrograms of the first batch of LCMS acetonitrile of Merck, the second batch of LCMS acetonitrile of Merck and the acetonitrile finished product provided by Embodiment 3, namely FIG. 4 to FIG. 6, are locally enlarged when m/z is at the interval of 55-160 to obtain FIG. 7 to FIG. 9, and in this interval, the first batch of LCMS acetonitrile of Merck, the second batch of LCMS acetonitrile of Merck and the acetonitrile finished product provided by Embodiment 3 have little difference in the m/z peak types except for the intensity.

Figure 10:
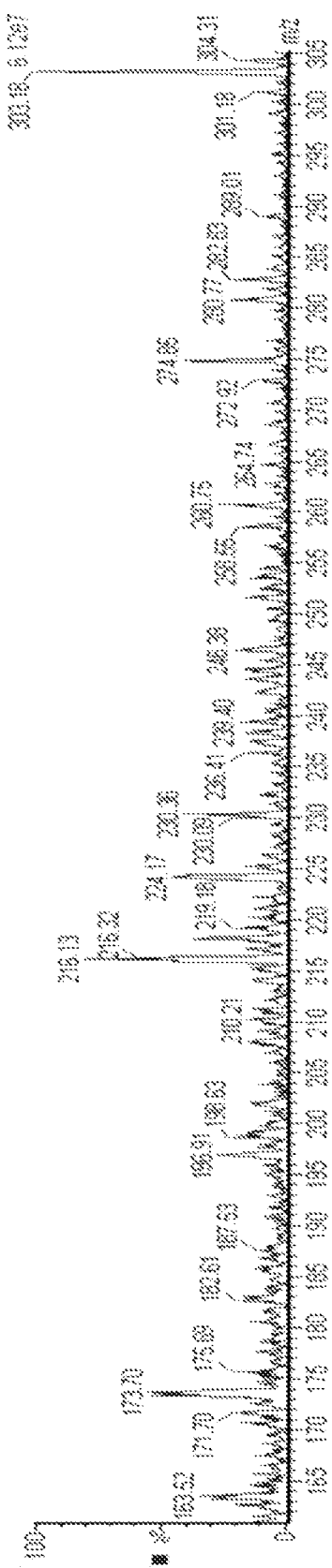
FIG. 10 is a partial enlarged view of m/z at an interval of 160-305 in FIG. 4.
Figure 11:
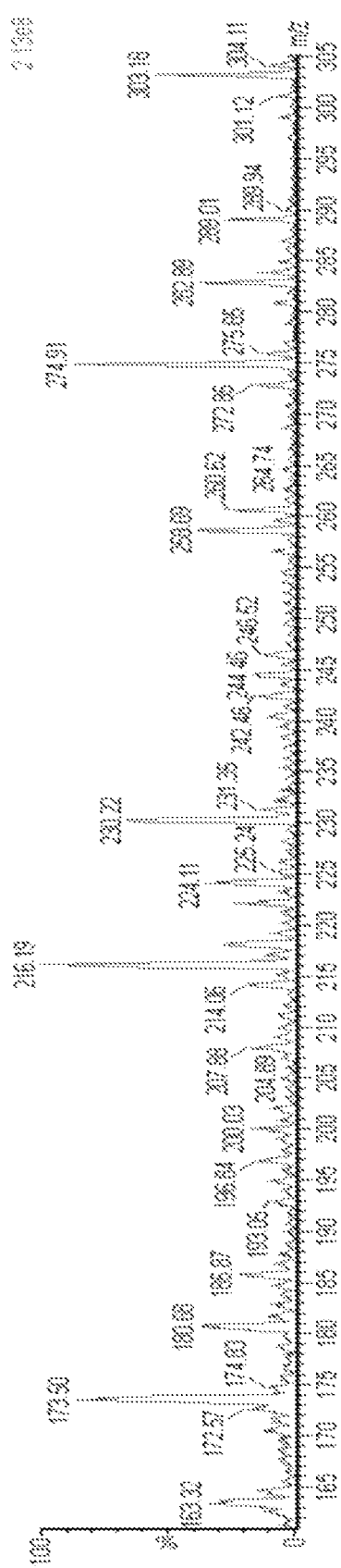
FIG. 11 is a partial enlarged view of m/z at an interval of 160-305 in FIG. 5.
Figure 12:
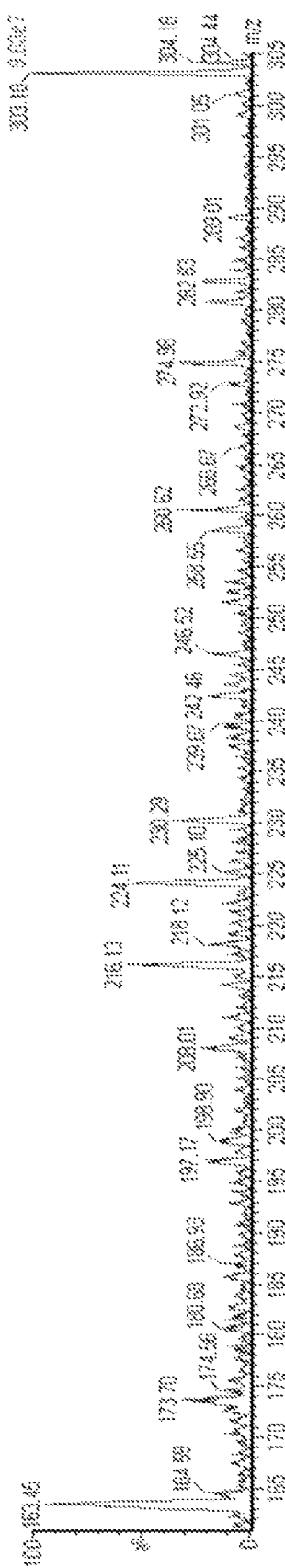
FIG. 12 is a partial enlarged view of m/z at an interval of 160-305 in FIG. 6.

The mass spectrograms of the first batch of LCMS acetonitrile of Merck, the second batch of LCMS acetonitrile of Merck and the acetonitrile finished product provided by Embodiment 3, namely FIG. 4 to FIG. 6, are locally enlarged when m/z is at the interval of 160-305 to obtain FIG. 10 to FIG. 12, and in this interval, the two batches of LCMS acetonitrile of Merck and the acetonitrile finished product provided by Embodiment 3 have difference in the peak intensity and type.

Figure 13:
FIG. 13 is a mass spectrum of an acetonitrile finished product provided by Embodiment 2.
Figure 14:
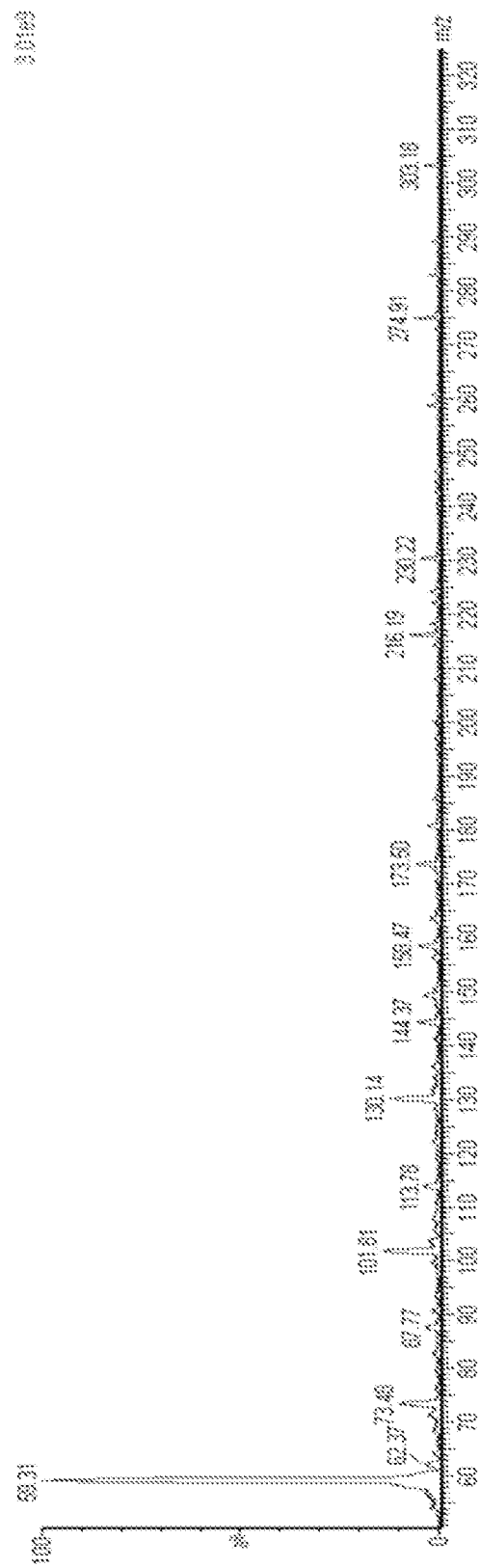
FIG. 14 is a mass spectrum of HPLC grade acetonitrile of Merck.

(2) Comparison between the acetonitrile finished product provided by the present invention and the HPLC grade acetonitrile of Merck FIG. 13 and FIG. 14 are mass spectrograms of the acetonitrile finished product provided by Embodiment 2 and the HPLC grade acetonitrile of Merck. On the whole, it is found that the m/z 59.2($CH_3CN^+NH^{4+}$) main peak, intensity of the acetonitrile finished product provided by Embodiment 2 is $3.31 \times e^9$, and the m/z 59.2($CH_3CN^+NH^{4+}$) main peak intensity of the HPLC grade acetonitrile of Merck is $3.01 \times e^9$.

Figure 15:
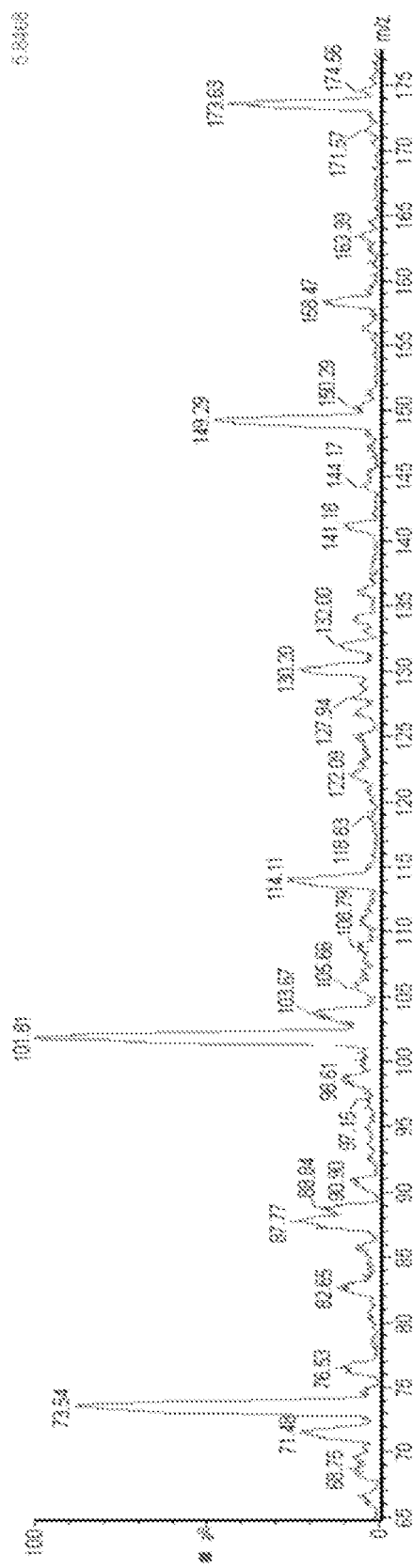
FIG. 15 is a partial enlarged view of m/z at an interval of 65-175 in FIG. 13.
Figure 16:
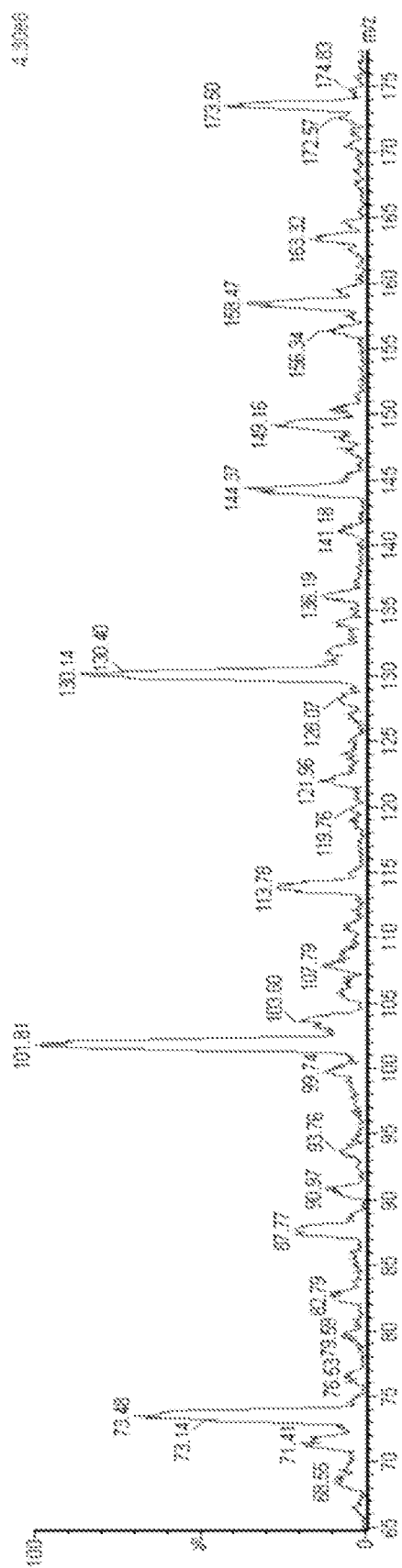
FIG. 16 is a partial enlarged view of m/z at an interval of 65-175 in FIG. 14.

The mass spectrograms of the acetonitrile finished product provided by Embodiment 2 and the HPLC grade acetonitrile of Merck, namely FIG. 13 to FIG. 14, are enlarged for comparison when m/z is at the interval of 65-175. As shown in FIG. 15 to FIG. 16, it is found that the peak intensity ($5.84 \times e^8$) of the acetonitrile finished product provided by Embodiment 2 is greater than the peak intensity ($4.30 \times e^8$) of the HPLC grade acetonitrile of Merck when the m/z is at 101, the peak intensity of the acetonitrile finished product provided by Embodiment 2 is less than the peak intensity of the HPLC grade acetonitrile of Merck when the m/z is at 130, and the peak intensities are similar at other m/z.

Figure 17:
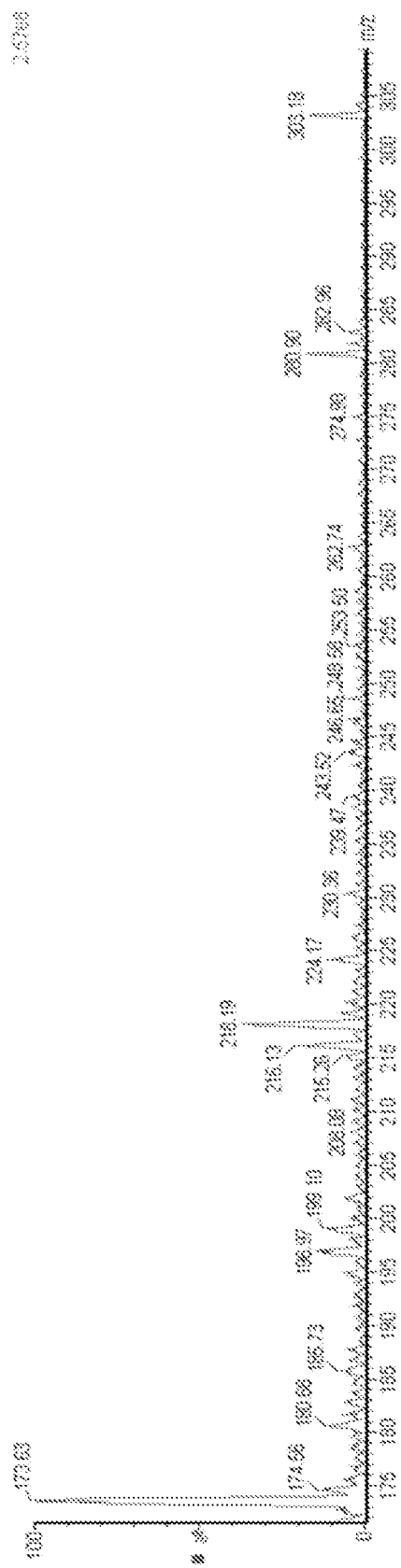
FIG. 17 is a partial enlarged view of m/z at an interval of 175-305 in FIG. 13.
Figure 18:
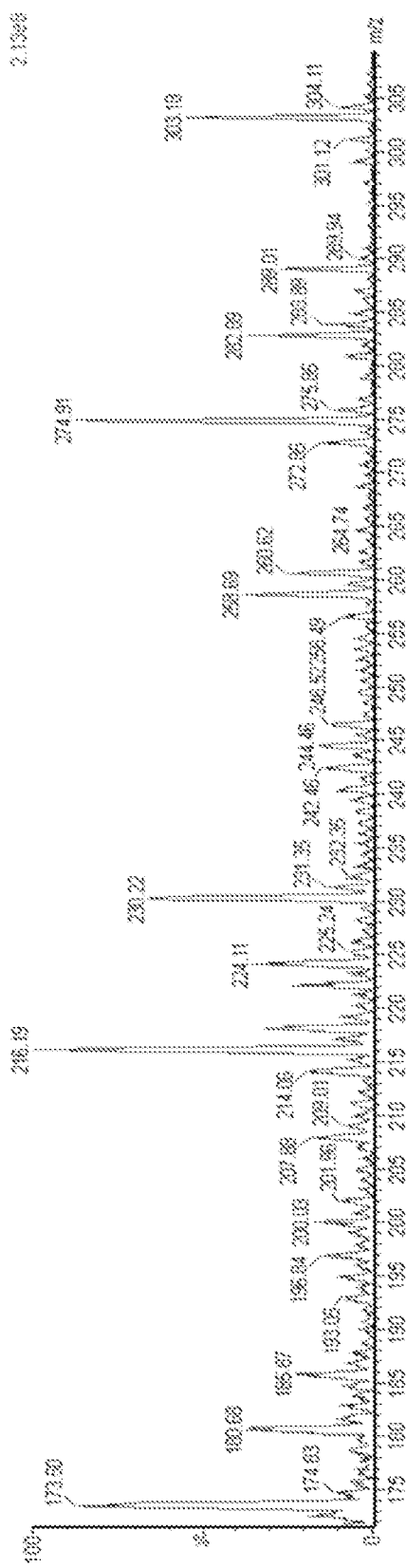
FIG. 18 is a partial enlarged view of m/z at an interval of 175-305 in FIG. 14.

The mass spectrograms of the acetonitrile finished product provided by Embodiment 2 and the HPLC grade acetonitrile of Merck, namely FIG. 13 to FIG. 14, are enlarged for comparison when m/z is at the interval of 175-305. As shown in FIG. 17 to FIG. 18, it is found that in this interval, the total intensity of the acetonitrile finished product provided by Embodiment 2 is less than that of the HPLC grade acetonitrile of Merck.

It can be seen from Table 1, Table 2 and the results of FIG. 2 to FIG. 18 that by the improved acetonitrile purification process provided by the present invention, the acetonitrile suitable for the ultrahigh performance liquid chromatography-mass spectrometer may be prepared and has high yield and purity.

The foregoing examples are merely illustrative and are used to explain some features of the method according to the present invention. The appended claims are intended to claim the conceivable scope as broad as possible, and the embodiments presented herein are illustrative only of implementation selected in accordance with a combination of all possible embodiments. Therefore, the intention of the applicant is that the appended claims will not be limited by the choice of the embodiments illustrating the features of the present invention. Some numerical ranges used in the claims are also inclusive of subranges therein and variations in these ranges should also be interpreted as being covered by the appended claims where possible.

What is claimed is:

1. An improved acetonitrile purification process, comprising the following steps:
   (1) adding an oxidizing agent into industrial acetonitrile containing impurities, water and acetonitrile to perform oxidation reaction, feeding the product into an adsorption and rectification tower for adsorption, and condensing the obtained tower top product of the adsorption and rectification tower to obtain a crude product, wherein a height of the adsorption and rectification tower is 7 to 30 m, and a pressure difference between the tower top and the tower bottom is 30 to 40 kPa;

(2) adding a drying agent into the crude product for drying, heating and entering a reflux rectifying tower for total reflux after removing water, removing heavy component impurities at the tower bottom of the reflux rectifying tower, extracting and condensing light component impurities and acetonitrile at the tower top of the reflux rectifying tower to obtain a semi-finished product; and (3) removing 20 to 40 kg of semi-finished products extracted initially so as to remove the light component impurities, and filtering the semi-finished product extracted later to obtain a finished product, wherein a light transmittance of the finished product in ultraviolet rays of 200 to 260 nm is greater than or equal to 95%;

wherein the number of the adsorption and rectification towers is two or three;

wherein a filter membrane of the filtration comprises a macromolecular filter membrane and an ion exchange filter membrane;

wherein the ion exchange filter membrane comprises an anion exchange filter membrane and a cation exchange filter membrane;

wherein in the step (3), 20 to 40 kg of semi-finished products extracted initially are removed so as to remove the light component impurities, and the semi-finished products extracted later are sequentially filtered by the macromolecular filter membrane with a pore diameter of 150 to 250 nm, the ion exchange filter membrane and the macromolecular filter membrane with a pore diameter of 5 to 8 nm to obtain the finished product.

2. The improved acetonitrile purification process according to claim 1, wherein in the oxidation reaction, the temperature is 80 to 90° C., the time is 1 to 6 h, and the pressure is 10 to 90 KPa.

3. The improved acetonitrile purification process according to claim 1, wherein the adsorption and rectification tower is filled with an adsorbent, a screen size of the adsorbent being 5 to 6 mm.

4. The improved acetonitrile purification process according to claim 1, wherein the flow of the total reflux is 10 to 100 kg/h, and the time is 2 to 10 h.

5. The improved acetonitrile purification process according to claim 4, wherein the extracted flow is 10 to 30 kg/h, and the reflux ratio is (1-2):1.

6. The improved acetonitrile purification process according to claim 1, wherein the oxidizing agent of the present invention accounts for 0.1-1 wt % of the industrial acetonitrile;

the oxidizing agent is a mixture of potassium superoxide, potassium hydroxide and sodium hydroxide with a weight ratio of 1:(4-6):(6-10).

7. The improved acetonitrile purification process according to claim 1, wherein the adsorption and rectification tower is filled with an adsorbent, and a screen size of the, adsorbent is 5 to 6 mm; The adsorbent suitable for the present invention is activated carbon.

8. The improved acetonitrile purification process according to claim 1, wherein in the step (2), a drying agent was added into a crude product was added for drying, and after water was removed, the crude product was heated to 80-90° C. to enter the reflux rectifying tower for total reflux.

9. The improved acetonitrile purification process according to claim 1, wherein the macromolecular filter membrane is a polytetrafluoroethylene filter membrane; the cationic filter membrane is the polytetrafluoroethylene sulfonated cationic filter membrane; the anion exchange filter membrane is the polytetrafluoroethylene anionic filter membrane.

\* \* \* \* \*